United States Patent [19]

Gander et al.

[11] 4,364,924

[45] Dec. 21, 1982

[54] ALKALI METAL SALTS OF POLY(VINYLBENZOIC ACID) AS DENTAL PLAQUE BARRIER AGENTS

[75] Inventors: Robert J. Gander, Whitehouse; Carl J. Buck, Berkeley Heights; Tibor Sipos, Lebanon, all of N.J.

[73] Assignee: Johnson & Johnson Products, Inc., New Brunswick, N.J.

[21] Appl. No.: 172,495

[22] Filed: Jul. 25, 1980

[51] Int. Cl.³ .................. A61K 7/16; A61K 31/74; A61K 31/19; C08F 30/04
[52] U.S. Cl. ........................... 424/49; 424/78; 424/317; 433/202; 526/240
[58] Field of Search .................... 424/49–56, 424/78; 528/230; 526/240; 433/202

[56] References Cited

U.S. PATENT DOCUMENTS

| | | | |
|---|---|---|---|
| 2,783,279 | 2/1957 | Chiddix | 424/49 |
| 3,385,905 | 5/1968 | Smith et al. | 260/505 R |
| 3,429,963 | 2/1969 | Shedlovsky | 424/56 |
| 4,138,477 | 2/1979 | Gaffar | 424/52 |
| 4,139,608 | 2/1979 | Schreiber | 424/49 |
| 4,238,476 | 12/1980 | Harvey | 424/56 |

FOREIGN PATENT DOCUMENTS 1072413  2/1980  Canada .

*Primary Examiner*—Douglas W. Robinson

[57] ABSTRACT

Compositions and methods for preventing the attachment of dental plaque to the surfaces of the teeth of mammals comprises certain alkali metal salts of poly(vinylbenzoic acid) in pharmaceutically acceptable vehicles, and the periodic applications thereof to teeth.

4 Claims, No Drawings

ALKALI METAL SALTS OF POLY(VINYLBENZOIC ACID) AS DENTAL PLAQUE BARRIER AGENTS

TECHNICAL FIELD

This invention relates to oral hygiene compositions and methods using such compositions to prevent attachment of bacteria to teeth. More particularly it relates to certain alkali metal salts of poly(vinylbenzoic acid) that have been found useful in inhibiting the agglutination of oral microbes on teeth.

BACKGROUND ART

The prevention of the deposition of dental plaque on teeth is a highly desired result. Dental plaque results when cariogenic bacteria aggregate in colonies on the surface of teeth and form a tenacious deposit thereon. The presence of plaque on teeth is believed to be a precursor to development of gingivitis, dental caries and periodontal disease.

While many attempts have been made to control the effects of cariogenic bacteria and the dental plaque they produce, for example, fluoride, flossing, brushing, etc., treatments, these are typically directed to either counteracting the secondary effects of plaque on the teeth and gums, or to the removal of plaque that is already formed on and adhering to the teeth and surrounding tissue. Such treatments are not, however, entirely successful, and must be supplemented with periodic treatment by dental professionals. To date, there is no commercially feasible home treatment method for preventing the formation of plaque or its adhesion to teeth.

The Invention

Certain alkali metal salts of poly(vinylbenzoic acid) have been found to inhibit the deposition of dental plaque onto human teeth when applied from various dentifrice formulations, mouth rinses, or other oral hygiene procedures. These hydrophilic polymers are substantially soluble in water or water/organic solvent vehicles and have good film forming characteristics. While the mechanism of action of the hydrophilic polymeric films in retarding plaque deposition is not known with absolute certainty, it is presumed that the films of anionically-charged polymers deposited on teeth effect a mutual repulsion between the negatively charged polymer film and the negatively charged microorganisms responsible for plaque generation. The polymeric salts of this invention are especially effective as components of dentifrices and other oral hygiene preparations in reducing dental plaque deposition on teeth.

The hydrophilic, polymeric salts found useful for dental plaque control in accordance with the present invention are essentially alkali metal salts of the homopolymers of vinylbenzoic acid, wherein the repeating unit of the polymer is represented by structure (A),

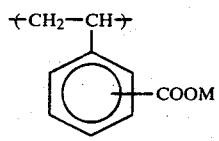

(A)

where M is selected from the group consisting of sodium, potassium, and lithium.

The poly(vinylbenzoic acid) polymers required as intermediates for the preparation of the salts of structure (A) are readily prepared by the free radical polymerization of vinylbenzoic acid monomers, typified by the 4-vinylbenzoic acid available from Pfaltz and Bauer. Neutralization of the poly(vinylbenzoic acid) polymers with alkali metal hydroxides, or addition of at least stoichiometric quantities of an alkali metal oxide, carbonate, chloride, nitrate, acetate, or sulfate, suffices to produce the polymeric salts of this invention. If desired, the aqueous solutions of the polymeric salts can be purified by dialysis and the dialyzed polymer solution freeze-dried, spray-dried, or evaporated to afford the polymeric salts in the solid form.

The alkali metal salts of the poly(vinylbenzoic acid) polymers of this invention are highly effective in reducing the deposition of plaque during in vitro testing. For example, sodium poly(4-vinylbenzoate) prepared from poly(4-vinylbenzoic acid) exhibited a 91% reduction in the deposition of plaque when tested. The in vitro test procedure employed begins with growth of plaque in small jars containing sterilized trypticase media that has been supplemented with sucrose. Typically, ten jars are individually inoculated with 0.5 ml of unpooled freshly collected human plaque from 10 subjects. In a control series, a presterilized glass slide or an extracted human tooth is inserted into each jar. In the test series, the tooth or glass slide is pretreated with a 1% solution of the test compound (dissolved in water or other vehicle), allowed to dry in order to deposit a thin film of the compound on the surface, and the glass slide or tooth placed in the growth media. The jars are incubated under anaerobic conditions for two days at 37° C. The tooth or glass slide is removed, air dried, and stained with 0.15% FD&C #3 red dye solution to reveal the accumulated plaque deposits. The tooth or glass slide is scored for plaque density on a 0 to 5 scale. Plaque barrier activity is reported as the % of average plaque reduction, as compared to appropriate controls for ten subjects.

EXAMPLE 1

Sodium poly(4-vinylbenzoate)

A suspension of 4.0 g (0.027 mole) 4-vinylbenzoic acid and 0.04 g azobisisobutyronitrile in 25 ml. benzene was heated under nitrogen at 80° C. for about 8 hours, during which time heavy precipitation of polymer took place. The suspension was cooled to room temperature, diluted with 25 ml. benzene, and filtered to give 4.0 g of poly(4-vinylbenzoic acid).

A solution of 1.6638 g of the poly(4-vinylbenzoic acid) in 30 ml. methanol was adjusted from pH 2.5 to pH 11.0 with 23.3 ml. 0.480 N methanolic sodium hydroxide. The resultant solution was solvent stripped to white solids of sodium poly(4-vinylbenzoate). The NMR and IR spectra were consistent with the structure of the polymeric salt.

The plaque barrier oral compositions of this invention may comprise any conventional pharmaceutically acceptable oral hygiene formulation that contains (and is compatible with) an effective amount of a plaque barrier agent as defined herein. Such formulations include, for example, mouthwashes, rinses, irrigating solutions, abrasive and nonabrasive gel dentifrices, denture cleansers, coated dental floss and interdental stimulator coatings, chewing gums, lozenges, breath fresheners, foams and sprays.

The plaque barrier agents may be present in these formulations in effective concentrations generally in the range of from about 0.05 weight percent to as much as 30 weight percent or the limit of compatibility with the vehicle. However, no advantage will be derived from concentrations in excess of about 20 weight percent. A preferred concentration range for the plaque barrier agents in the formulations of the invention is from about 0.5 to about 10 weight percent. A more preferred range is from about 2 to about 8 percent by weight, about 5% being the presently most preferred concentration in a nonabrasive gel vehicle.

The pH of these plaque barrier preparations should be between pH 5.0 and 10.0, preferably between pH 5.0 and 8.0, more preferably between about pH 6.0 and 7.5. Lower pH than 5.0 is undesirable because of the possible enhancement of enamel demineralization.

Suitable conventional pharmaceutically acceptable vehicles that can be employed with the plaque barrier agents to prepare the barrier compositions of this invention may comprise water, ethanol; such humectants as polypropylene glycol, glycerol and sorbitol; such gelling agents as cellulose derivatives, for example, Methocel, carboxymethylcellulose (CMC 7MF) and Klucel HF, polyoxypropylene/polyoxyethylene block copolymers, for example, Pluronic F-127, Pluronic F-108, Pluronic P-103, Pluronic P-104, Pluronic P-105, and Pluronic P-123, colloidial magnesium aluminosilicate complexes such as Veegum, and mucoprotein thickening agents such as Carbopol 934; gel stabilizers such as the silicon dioxides, for example, Cab-O-Sil M5, and polyvinylpyrrolidone; sweeteners such as sodium saccharin; preservatives such as citric acid, sodium benzoate, cetylpyridinium chloride, potassium sorbate, methyl and ethyl parabens; detergents such as sodium lauryl sulfate, sodium cocomonoglyceride sulfonate, sodium lauryl sarcosinate and polyoxyethylene isohexadecyl ether (Arlasolve 200) and approved colors and flavors.

The following specific examples will serve further to illustrate the plaque barrier compositions of this invention.

EXAMPLE A—Mouthwash Solution

| | |
|---|---|
| Barrier Agent | 0.5-2.0 % w/w |
| Glycerol (humectant) | 6.0 |
| Pluronic F-108 | 1.0 |
| Sodium saccharin (sweetener) | 0.3 |
| Deionized Water | q.s. |
| Flavors | 1.0 |
| | 100.0 |

EXAMPLE B—Mouthwash Solution

| | |
|---|---|
| Plaque Barrier Agent | 0.5-3.0 % w/w |
| Ethanol, USP | 15.0 |
| Pluronic F-108 (foaming agent) | 2.0 |
| Glycerol (humectant) | 10.0 |
| Sorbitol (humectant) | 10.0 |
| Sodium saccharin (sweetener) | 0.2 |
| Deionized Water | q.s. |
| Flavors | 0.2 |
| | 100.0 |

EXAMPLE C—Abrasive Dentifrice Gel

| | |
|---|---|
| Plaque Barrier Agent | 2.0-10.0 % w/w |
| Fumed Silica (abrasive) | 55.0 |
| Sodium Lauryl Sulfate (detergent) | 1.5 |
| Glycerol (humectant) | 10.0 |
| Carboxymethylcellulose (gelling agent) | 2.0 |
| Sodium saccharin (sweetener) | 0.2 |
| Sorbitol (humectant) | 10.0 |
| Flavors | 1.0 |
| Deionized Water | q.s. |
| Preservative | 0.05 |
| | 100.0 |

EXAMPLE D—Chewing Gum

| | |
|---|---|
| Plaque Barrier Agent | 1.0-11.0 % w/w |
| Gum Base | 21.3 |
| Sugar | 48.5-58.5 |
| Corn Syrup (Baume 45) | 18.2 |
| Flavors | 1.0 |
| | 100.0 |

EXAMPLE E—Nonabrasive Gel Dentifrice

| | |
|---|---|
| Plaque Barrier Agent | 0.05-30.0 % w/w |
| Sorbistat (preservative) | 0.15 |
| Deionized Water | q.s. |
| Silicon Dioxide (gel stabilizer) | 1.0 |
| Pluronic F-127 (gelling agent) | 20.0 |
| Sodium Saccharin | 0.2 |
| Flavors | 1.5 |
| | 100.0 |

EXAMPLE F

The following formulation illustrates a presently preferred nonabrasive gel composition containing a barrier agent in accordance with the present invention.

| Ingredients | % w/w |
|---|---|
| Distilled Water | q.s. |
| Sodium Saccharin (sweetener) | 0.20 |
| Sodium Benzoate (preservative) | 0.30 |
| FD & C Blue #1 (0.1% aq. soln.) | 0.27 |
| D & C Yellow #10 (0.5% aq. soln.) | 0.50 |
| Gelling agent | 18.00 |
| Glycerol (Humectant) | 20.00 |
| Cab-O-Sil M5 (Silicon Dioxide) | 1.00 |
| Plaque Barrier Agent | 5.00 (dry basis) |
| Flavor | 0.80 |
| | 100.0 |

While the details of preparing all of the above formulations are well within the skill of the art, a suggested procedure for preparing the gel formulation of this example will be described for completeness.

In a first container the water, sodium saccharin, sodium benzoate and dyes are mixed. Then the container is put into an ice bath. When the temperature reaches 6° C., the gelling agent is added and the contents mixed slowly until the gelling agent is dissolved. Then the solution is heated to 70° C.

Into a second container is added the glycerin. Then the Cab-O-Sil M5 is sprinkled in with mixing. Then the plaque barrier agent is added and mixing continued to a smooth paste. The paste is then heated in a water bath with mixing to a temperature of 70° C.

The contents of the first container are added to the second container and blended together until the batch is homogenous while maintaining a 70° C. temperature. Then the flavoring is added, all mixing is stopped, and the formulation allowed to settle for approximately one hour. If necessary to remove air bubbles, overnight refrigeration may be employed.

These compositions are preferably employed from one to three times daily in a routine oral hygiene program to prevent the attachment of plaque to the teeth.

Variations can, of course, be made without departing from the spirit or scope of the invention.

We claim:

1. An oral hygiene composition comprising an effective amount for preventing deposition of dental plaque or teeth of an alkali metal salt of a homopolymer of vinylbenzoic acid having repeating units of structure (A),

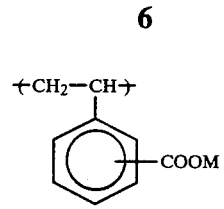

wherein M is selected from the group consisting of lithium, sodium, and potassium, in a pharmaceutically acceptable oral hygiene vehicle compatible with said polymer.

2. A method of preventing deposition of dental plaque on teeth comprising periodically applying to the teeth a composition of claim 1.

3. The method of claim 2 wherein said composition is applied from about 1 to about 3 times per day.

4. The composition of claim 1 in the form of an oral hygiene formulation selected from the group consisting of mouthwashes, mouthrinses, irrigating solutions, abrasive gel dentifrices, non-abrasive gel dentifrices, denture cleansers, coated dental floss, coated interdental stimulators, chewing gums, lozenges, breath fresheners, foams and sprays.

* * * * *